United States Patent
Schultz et al.

[19]

[11] Patent Number: 6,110,259
[45] Date of Patent: Aug. 29, 2000

[54] SMOKE EVACUATION SYSTEM

[75] Inventors: Leonard S. Schultz; Jeffrey K. Drogue, both of Minneapolis, Minn.

[73] Assignee: JLJ International, Inc., Minneapolis, Minn.

[21] Appl. No.: 09/046,265

[22] Filed: Mar. 23, 1998

Related U.S. Application Data

[60] Provisional application No. 60/066,331, Nov. 21, 1997.

[51] Int. Cl.⁷ .......................... B01D 39/00; B01D 50/00
[52] U.S. Cl. ........................ 95/273; 95/286; 55/385.1; 55/486; 55/503; 604/35
[58] Field of Search ................. 55/385.1, 385.2, 55/418, 486, 503, 505, 385.4; 604/35, 45, 264; 95/273, 286

[56] References Cited

U.S. PATENT DOCUMENTS

| | | |
|---|---|---|
| 3,952,727 | 4/1976 | Nolan . |
| 4,083,706 | 4/1978 | Wiley ........................................ 55/385 |
| 4,211,224 | 7/1980 | Kubach et al. . |
| 4,294,594 | 10/1981 | Sloane, Jr. et al. . |
| 4,449,970 | 5/1984 | Bevan et al. . |
| 4,451,258 | 5/1984 | Jensen ...................... 604/333 |
| 4,735,603 | 4/1988 | Goodson et al. . |
| 4,874,513 | 10/1989 | Chakraborty et al. ............. 210/321.84 |
| 4,906,261 | 3/1990 | Mahajer .................................. 55/385.1 |
| 4,963,134 | 10/1990 | Backscheider et al. . |
| 4,986,839 | 1/1991 | Wertz et al. . |
| 5,199,944 | 4/1993 | Cosmescu . |
| 5,242,474 | 9/1993 | Herbst et al. . |
| 5,423,779 | 6/1995 | Yeh . |
| 5,578,000 | 11/1996 | Greff et al. . |
| 5,597,385 | 1/1997 | Moerke ..................................... 55/473 |
| 5,626,568 | 5/1997 | Yeh et al. . |
| 5,674,219 | 10/1997 | Monson et al. ........................... 604/45 |
| 5,709,675 | 1/1998 | Williams ................................... 604/35 |
| 5,779,662 | 7/1998 | Berman .................................... 604/35 |
| 5,824,138 | 10/1998 | Taylor, III ............................... 95/288 |

*Primary Examiner*—David A. Simmons
*Assistant Examiner*—Robert A. Hopkins
*Attorney, Agent, or Firm*—Dorsey & Whitney LLP

[57] ABSTRACT

A smoke evacuating system for use during surgical procedures, particularly minimally invasive procedures involving the use of a laser or cautery at a surgical site having an associated higher than ambient pressure, wherein the system includes a filter with a site side and an outlet side and a fluid conduit extending between the surgical site and the filter. The filter exhibits low resistance or a low pressure drop and resists fluid flow, whereby the higher than ambient pressure is not substantially diminished and generates a fluid flow in the fluid flow path tending to carry smoke to and through the filter.

18 Claims, 3 Drawing Sheets

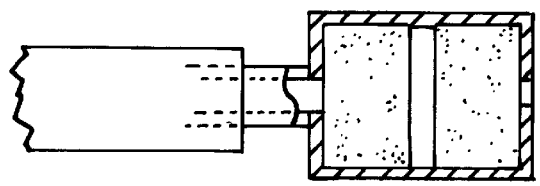
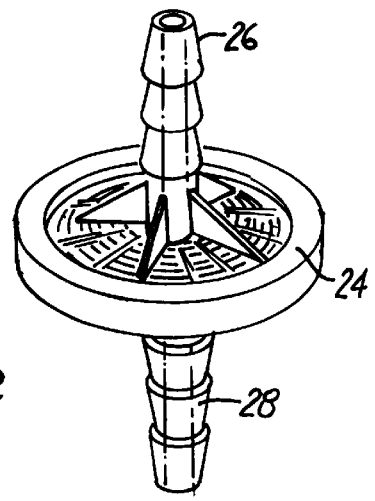
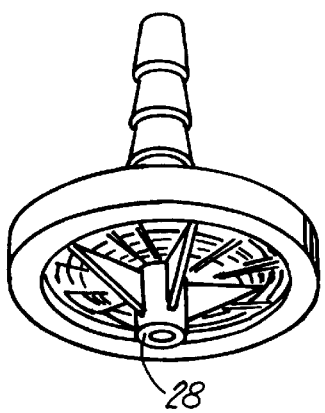
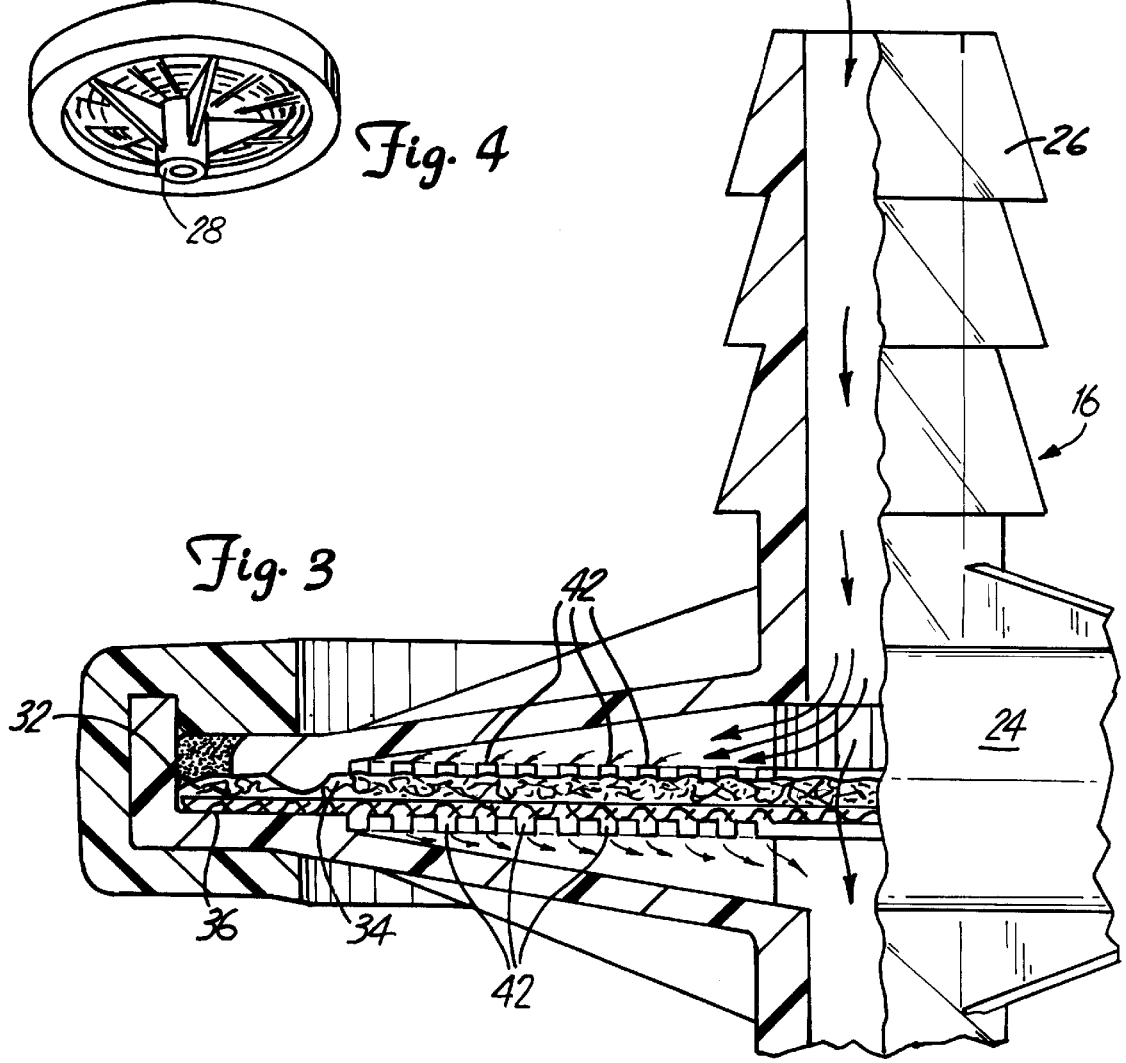

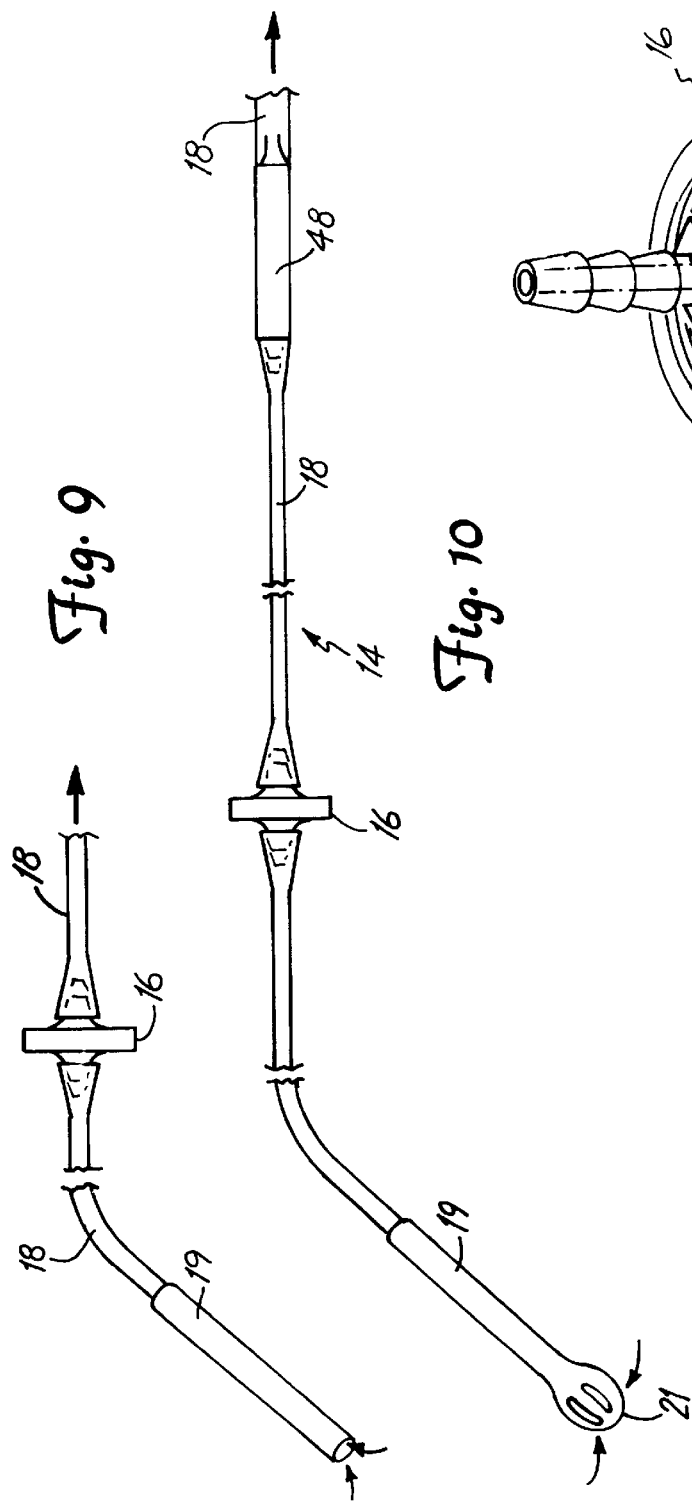

SMOKE EVACUATION SYSTEM

The present application claims the priority benefit of a provisional application Ser. No. 60/066,331, filed Nov. 21, 1997.

BACKGROUND OF THE INVENTION

1. Field of the Invention

The present invention relates to smoke removal and filtering and, more particularly, to a smoke evacuation system for use in surgical procedures, including minimally invasive surgical procedures such as laparoscopy during which cautery or a laser is used.

2. Description of Related Art

U.S. Pat. No. 5,578,000 (Greff et al.) discloses a smoke evacuation system including a trocar having a working channel, a stopcock or valve communicating with the channel, a source of wall vacuum, a fluid conduit connected between the stopcock of the trocar and the source of wall vacuum, a first filter for applying a first reduction in suction and separating smoke into its components and a residual gas, and a flow restriction to generate a second reduction in suction. The flow restriction is along a passage formed by the conduit, the filter and working channel.

Greff et al. note that smoke has been handled by simply allowing it to escape into the operating room, thereby subjecting the surgeon and staff to contaminants. They recognize that closed, recirculating systems involving two trocars have been used, as have probes which are inserted through a trocar, but that such systems do not adequately solve the problems associated with smoke and the removal thereof, e.g., contamination, smell and impaired visibility of an surgical site.

Other problems inadequately addressed by currently available evacuation systems are loss of the pressure in the pneumoperitoneum, and/or tissue drying, particularly if pressure loss is compensated for by increasing insufflation gas flow.

While the smoke evacuation system disclosed in the Greff et al. patent may be well suited for its intended purpose, it would be advantageous if the dependency on a remote, "in-wall" vacuum source could be eliminated thereby reducing the cost and complexity of the system.

SUMMARY

The present invention provides an improvement over currently known smoke evacuation systems, methods and techniques, including laparoscopic smoke evacuation systems such as the system disclosed in the Greff et al. patent.

In one embodiment, the present invention provides a smoke evacuating system for use during surgical procedures comprising a filter for operable coupling to a surgical site, said filter exhibiting a pressure drop ranging from approximately 0.5 to 20 mm/Hg, with a preferred pressure drop ranging from approximately 1 to 3 mm/Hg. The filter may be coupled directly to the patient.

In another embodiment, the present invention provides a smoke evacuating system for use during surgical procedures, particularly minimally invasive procedures involving a surgical site having an associated higher than ambient pressure, wherein the system comprises a filter with a inlet side (the side generally closest to the surgical site) and an outlet side and a fluid conduit extending between the surgical site and the filter. The fluid conduit defines a substantially unobstructed fluid flow path between the surgical site and filter, and the higher than ambient pressure and a pressure drop associated with the filter generate and enable a fluid flow in the fluid flow path, the filter causing a low pressure drop (i.e., pressure differential from side to side) in the fluid flow from the inlet side to the outlet side.

In yet another embodiment, the present invention provides a smoke evacuating system for use during surgical procedures, particularly minimally invasive procedures, including a conduit for operable coupling to a surgical site, said conduit operably carrying a filter exhibiting a pressure drop ranging from approximately 1 to 3 mm/Hg and defining a substantially unobstructed fluid flow path between the surgical site and the filter. The conduit may include a connector for being connected to a trocar or other tubular member. An on/off valve may be incorporated to control the flow of fluid through the conduit, whereby, when the valve is open, the flow path from the surgical site to the filter is substantially unobstructed.

An advantage of the present invention is that it eliminates dependency on a built-in, in wall vacuum source. It does not require high vacuum suction and the requisite high resistance filters or combination of flow restrictors or reducers and filters. Further, it simplifies smoke evacuation and filtering by eliminating the need for multiple, in-line structures (filters, resistors, etc.) for stepping down or reducing suction.

While the present invention may be used in surgical procedures, it may also be used in industry to remove smoke and/or chemicals from workstations. For example, it might be used at or adjacent to chip or electronic equipment manufacturing stations to reduce workers' exposure to smoke produced as connections are formed. Similarly, it might be used to reduce exposure to etching chemicals.

A feature of the present invention is a balanced smoke evacuation system wherein a filter with a relatively low pressure drop performs a filtering function and a flow regulating function, helping to preserve the pressure at or in a pressurized surgical site such as a laparoscopy with a pneumoperitoneum while providing for sufficient flow therefrom to remove smoke from the site, thereby reducing the need for substantial or constant reinsufflation of the surgical site.

Another embodiment of the invention includes an elbow member adapted to be coupled between a trocar and the conduit to position the conduit to reduce any potential inconvenience to the surgeon and/or staff during a procedure.

An advantage of the smoke evacuation system of the present invention is that it provides for the intra-operative evacuation and filtration of smoke from a pressurized surgical site, e.g., the abdominal cavity, without requiring suction and without rapidly exhausting the pressurizing gas or causing a substantial pressure reduction at the pressurized surgical site. Other advantages are that the invention does not require an operator, it continuously removes smoke from the pressurized cavity (once the valve in valved embodiments is opened) to improve visibility without venting, it reduces operating time, it eliminates surgical smoke from the operating room, thereby reducing the health risk stemming from exposure to such smoke, it eliminates the need to apply suction to a patient thereby reducing potential tissue damage, and it is inexpensive.

Other features and advantages of the smoke evacuating apparatus and method of the present invention will become more fully apparent and understood with reference to the following description and drawings, and the appended claims.

BRIEF DESCRIPTION OF THE DRAWINGS

FIG. 2 depicts the filter of one embodiment of the present invention.

FIG. 3 depicts a portion of the filter of FIG. 2 in cross section.

FIG. 4 depicts another embodiment of the filter.

FIG. 8 depicts another embodiment of the filter.

FIG. 9 depicts another embodiment of the smoke evacuation system of the present invention.

FIG. 10 depicts another embodiment of the smoke evacuation system of the present invention.

FIG. 11 depicts the filter of one embodiment of the present invention coupled to a surgical site.

DESCRIPTION

The accompanying Figures depict embodiments of the smoke evacuation apparatus or system of the present invention, and features and components thereof. With regard to means for fastening, mounting, attaching or connecting the components of the present invention to form the apparatus as a whole, unless specifically described otherwise, such means are intended to encompass conventional fasteners such as machine screws, machine threads, snap rings, hose clamps such as screw clamps and the like, rivets, nuts and bolts, toggles, pins and the like. Components may also be connected by friction fitting, or by welding or deformation, if appropriate. Unless specifically otherwise disclosed or taught, materials for making components of the present invention are selected from appropriate materials such as metal, metallic alloys, natural or synthetic fibers, plastics and the like, and appropriate manufacturing or production methods including casting, extruding, molding and machining may be used.

Any references to front and back, right and left, top and bottom, upper and lower, and horizontal and vertical are intended for convenience of description, not to limit the present invention or its components to any one positional or spacial orientation.

Figure 1:
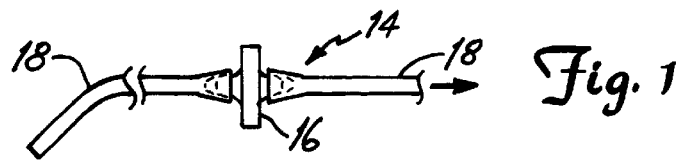
FIG. 1 depicts one embodiment of the smoke evacuation system of the present invention.
Figure 5:
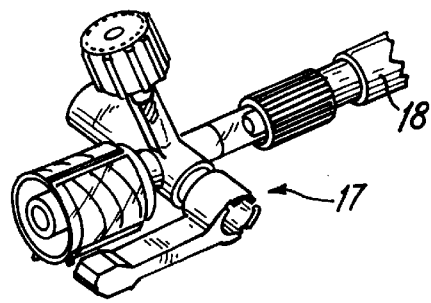
FIG. 5 depicts a connector stopcock or valve for use in the smoke evacuation system of the present invention.

Referring to the Figures, particularly FIG. 1, the present invention provides a smoke evacuating system 14 for use during surgical procedures. The system 14 includes a filter 16 and a generally flexible fluid conduit 18 connected to the filter 16. The conduit 18 may be provided in one or more pieces. The system 14, particularly the end of the conduit 18, may include an integral or attachable male or female connector (of the type well known in the art) for facilitating the connection of the conduit 18 to the exhaust port or vent valve of a trocar, or the system 14 may include a Leur lock-type valve 17 (see FIG. 5) operably coupled to the conduit 18, and it may include a generally tubular member 20, such as a typical well known trocar with an exhaust port (not shown).

Referring to FIG. 3, the filter 16 comprises a housing 24 with an inlet connector 26 and an outlet connector 28. Stepped hose barb type connectors may be used, as depicted in the Figures. The housing 24 may be made from polypropylene or other suitable material. The housing 24 contains the filter media 32, which comprises two thin, flat circular, disk shaped layers 34, 36. One layer 36, the layer adjacent to the outlet connector 28, is formed of 0.2 $\mu$m hydrophobic 200 mg/square cm PTFE, and the other layer 34 is made of a 200 g/square m 50% cellulose/carbon fiber blend. The layers 34, 36 are immediately adjacent to each other and each has a large surface area. Together, they form a filter media 32 having a surface area generally corresponding to its filtration area, i.e., approximately 7.5 square cm, approximately 100 times larger than the cross sectional area of the lumen of the depicted ¼ inch conduit 18. Although a disk-shaped filter is depicted, other shapes may be used as long as a pressure drop suitable for low flow, low pressure filtering is achieved. The filter 24, one or both layers, may be designed to exhibit a "change filter" color change indicative that useful life of the filter is over or nearly over. The odor removing layer 34 may be formed by or incorporate carbon or charcoal based material, or a diatomaceous earth material or other odor removing or reducing agent may be used.

The filter media 32 is potted in the housing 24. The housing 24 has a inlet manifold 40 and an outlet manifold 42. On each side of the filter media 32, in the respective manifolds, the housing has a plurality of annular grooves 42. The housing 24 may be formed around the filter media 32, or it may be formed in pieces which are joined to pot the media 32. An alternative, button or rivet-like embodiment of the filter 16, wherein the outlet 28 is substantially reduced to an outlet port 28', is depicted in FIG. 4. This embodiment of the filter 16 may be carried at the free end of the conduit 18 or it, or a similar embodiment with a suitable protruding inlet connector for extending through the abdominal wall, may be coupled directly to the abdomen of a patient, for example, through a needle stick or other suitable opening.

The system 14 provides a substantially unobstructed fluid flow path through the fluid conduit 18 between a valve 18 and filter 16 and, when the valve 18 is open, between a pressurized surgical site "S" and the filter 16. The filter 16 provides flow regulation of a fluid (insufflation gas carrying smoke) flowing along the fluid flow path in that it provides resistance to flow, whereby flow rates in some embodiments range from one (1) to four (4) liters/minute and, in other embodiments, range from 1 to 3.8 liters/minute. The filter 16 exhibits or has an associated pressure drop from one side to the other of from approximately one-half (0.5) to twenty (20) mm of mercury, with a pressure drop of from approximately two (2) to three (3) mm of mercury being preferred in another embodiment, and a pressure drop of approximately one (1) mm of mercury being preferred in yet another embodiment. The latter pressure drops correspond generally to flow rates of 1.8 liters/minute and 3.6 to 3.8 liters/minute, respectively. Higher pressures and/or lower pressure drops will produce higher correlative flow rates, and the filter 16 may be available in several specifications to be matched with the patient, function or procedure involved. The size and length of the fluid conduit or tube 18 may be varied to assist in providing desired flow characteristics (approximately 1.0 to 30 liters per minute) in conjunction with the resistance or pressure drop of the filter 16 of the present invention. In some embodiments, the tube 18 may be four to six feet in length, with a length of from 1.5 to 3.0 feet being preferred. If quarter inch tubing is selected, the lumen of the tube 18 typically would be 3 mm in diameter, but inner diameters ranging from 2 to 12 mm may be used. The parameters of diameter and length of tube 18, size of trocar (for one preferred example, 3 mm), and the resistance or pressure drop co associated with filter 16 may be relatively adjusted to accommodate different patients, surgical procedures and/or operating room settings, as long as adequate low pressure, low flow smoke filtering and odor removal is achieved. The present invention may be embodied in a completely disposable, single use unit or components thereof, e.g., the filter or tubing, may be disposable with other component reusable. Typically, the trocar 20 or tubular member to which the conduit 18 is coupled, either directly or through an exhaust port or valve, is grounded to eliminate any errant current.

Figure 7:
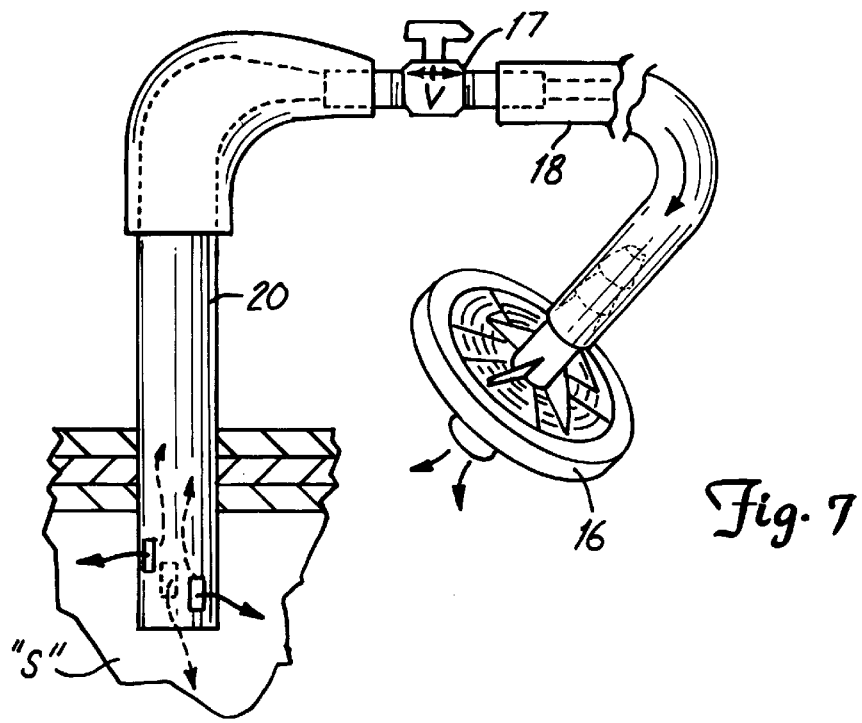
FIG. 7 depicts an elbow connector connecting a trocar and a valve connector.
Figure 6:
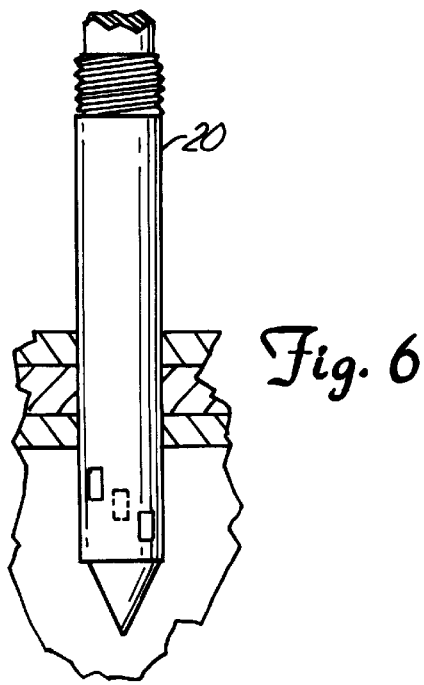
FIG. 6 depicts, largely representationally, a trocar (and obturator) of a type suitable for use with the present.

The present invention encompasses a method for evacuating smoke from a surgical site, particularly from a minimally invasive site such as a laparoscopy with a pneumoperitoneum. For example, for evacuating smoke from a surgical site in the abdominal cavity during a laparoscopic procedure, the method of the present invention comprises the steps of operably coupling a conduit 18 to the pneumoperitoneum, for example to the tubular member 21 (FIG. 7) extending from the pneumoperitoneum, and coupling a filter 16 having a low pressure drop there across to the conduit 18, whereby there is a substantially unobstructed, low volume fluid flow path between the pneumoperitoneum and the filter 18, whereby particulate material and odor are removed from the fluid. The fluid is induced to flow through the conduit 18 and filter 16 by the generally complementary pressure of the insufflating gas of the pneumoperitoneum and the pressure drop of the filter 16. In one embodiment, the flow may be controlled, e.g., initiated, stopped or reduced by incorporating a valve (such as a Leur lock valve (FIG. 5) or the like) with the conduit 18 or by using a valved trocar or the like.

The apparatus and method of the present invention may be used in laparoscopic procedure involving a pneumoperitoneum, i.e., a condition in which air or gas is collected or insufflated into the peritoneal cavity, but it also may be used in any other surgical procedure involving a substantially enclosed and/or pressurized surgical site such as thoracoscopy. Referring to FIG. 10, in one embodiment, the conduit 18 may be fitted with flow generating device 48 such as an in-line blower or impeller, which may be battery powered such as some commercially available models, for drawing air, smoke, particulate matter and contaminants into the conduit for filtration, whereby the invention may be used for "open" surgical procedures. In this embodiment, the selected flow generating device 48 may be located on either side of the filter 16, although positioning it on the outlet side of the filter 16 may protect it from contaminants and, in non-disposable embodiments, lengthen its useful life. The flow generating device 48 may be incorporated with the filter 16 itself, for example, in the outlet connector. With reference to FIGS. 9 and 10, for use in open site surgical procedures, the site or intake end of the conduit 18 may be expanded as at 19 and provided with a grille 21. In this embodiment the expanded end 19 may be, for example, inserted partially into a deep wound or connected to a patient's body near a surgical site (e.g., by using adhesive, straps, sutures or the like).

The present invention may be embodied in other specific forms without departing from the essential spirit or attributes thereof. It is desired that the embodiments described herein be considered in all respects as illustrative, not restrictive, and that reference be made to the appended claims for determining the scope of the invention.

What is claimed is:

1. A filter for use in surgical procedures, wherein the filter is adapted to be operably coupled to a pressurized surgical site and has a resistance such that it causes a fluid flow rate of from approximately 1 to 20 liters per minute when coupled to the pressurized surgical site, wherein a pressure drop of approximately 0.5 to 20 mm Hg is maintained from the surgical site to ambient air, and wherein the fluid flow is induced as a result of the pressure in the pressurized surgical site.

2. The filter according to claim 1, wherein the filter has a resistance such that it exhibits a pressure drop of approximately 2 to 3 mm Hg at a fluid flow rate of approximately 1.8 liters per minute when coupled to the pressurized surgical site.

3. The filter according to claim 2, wherein the filter comprises a particulate removing media and an odor removing media.

4. A smoke evacuating system for use during surgical procedures comprising a conduit adapted to be operably coupled to a pressurized surgical site and a filter adapted to be operably coupled to the conduit, said conduit forming a substantially unobstructed fluid flow path from the pressurized surgical site to the filter, said filter having a surgical site side and an outlet side, and causing an associated fluid flow rate through the filter at a maintained pressure drop from the surgical site side to the outlet side, wherein the fluid flow is induced as a result of the pressure in the pressurized surgical site.

5. The smoke evacuating system according to claim 4, wherein said filter causes a fluid flow rate of from approximately 1 to 20 liters per minute when the conduit and filter are coupled to the pressurized surgical site at a pressure drop ranging from approximately 0.5 to 20 mm Hg.

6. The smoke evacuating system according to claim 5, wherein said filter comprises a particulate removing media and an odor removing media.

7. A smoke evacuating system for use during minimally invasive surgical procedures involving a pressurized surgical site having an associated higher than ambient pressure, said system comprising a filter with a site side and an outlet side and a fluid conduit extending between the pressurized surgical site and the filter, said fluid conduit defining a substantially unobstructed fluid flow path between the pressurized surgical site and filter, said higher than ambient pressure generating a fluid flow in the fluid flow path, and said filter causing a fluid flow rate of from approximately 1 to 20 liters per minute when coupled to the pressurized surgical site at a pressure drop of from approximately 0.5 to 20 mm Hg from the site side to the outlet side, wherein the fluid flow is generated substantially by the pressure in the pressurized surgical site.

8. The filter according to claim 7, wherein the filter comprises a particulate removing media and an odor removing media.

9. The filter according to claim 8, wherein the filter has a surface area larger that the cross-sectional area of the fluid conduit.

10. The filter according to claim 8, wherein the filter causes a fluid flow rate of approximately 1.8 liters per minute at a pressure drop of approximately 2 to 3 mm Hg.

11. The filter according to claim 10, wherein the filter causes a fluid flow rate of from approximately 3.6 to 3.8 liters/minute at a pressure drop of approximately 1 mm Hg.

12. The smoke evacuation system of claim 7 consisting essentially of said filter and said fluid conduit.

13. A method for evacuating smoke from a pressurized chamber, the method comprising:

coupling a filter to a hole in the pressurized chamber, wherein the filter causes an associated fluid flow rate at a maintained pressure drop from the pressurized chamber to ambient air; and exhausting the smoke from the pressurized chamber through the filter by using air flow induced by the maintained pressure in the pressurized chamber.

14. The method of claim 13 further comprising coupling the filter to the chamber by using a fluid conduit.

15. The method of claim 13 wherein the filter causes a fluid flow rate of from approximately 1 to 30 liters per minute when coupled to the pressurized chamber at a pressure drop of from approximately 0.5 to 20 mm Hg.

16. A smoke evacuating system comprising a filter adapted to be operably coupled to a pressurized site, wherein the filter has a resistance such that it causes a fluid flow rate of from approximately 0.2 to 20 liters per minute when coupled to the pressurized site, wherein a pressure drop of approximately 0.5 to 30 mm Hg is maintained from the pressurized site to ambient air, and wherein the fluid flow is induced as a result of the pressure in the pressurized site.

17. The smoke evacuating system of claim 16, wherein the filter has a resistance such that it exhibits a pressure drop of approximately 2 to 3 mm Hg at a fluid flow rate of approximately 1.8 liters per minute when coupled to the pressurized site.

18. A smoke evacuating system for use during surgical procedures comprising a filter adapted to be operably coupled to a pressurized surgical site, the filter having a surgical site side and an outlet side, wherein the filter causes an associated fluid flow rate from the pressurized surgical site through the filter at a maintained pressure drop from the surgical site side to the outlet side, wherein the fluid flow is induced as a result of the pressure in the pressurized surgical site.

* * * * *

UNITED STATES PATENT AND TRADEMARK OFFICE
CERTIFICATE OF CORRECTION

PATENT NO. : 6,110,259
DATED : August 29, 2000
INVENTOR(S) : Leonard S. Schultz and Jeffrey K. Drogue Page 1 of 1

It is certified that error appears in the above-identified patent and that said Letters Patent is hereby corrected as shown below:

<u>Column 5,</u>
Line 1, reads "drop co associated" should be -- drop associated --

Signed and Sealed this

Twenty-first Day of May, 2002

Attest:

JAMES E. ROGAN
*Attesting Officer*     *Director of the United States Patent and Trademark Office*